United States Patent
Lorenzo

[19]

[11] Patent Number: 5,836,892
[45] Date of Patent: Nov. 17, 1998

[54] GUIDEWIRE WITH RADIOPAQUE MARKERS

[75] Inventor: Juan Lorenzo, Miami, Fla.

[73] Assignee: Cordis Corporation, Miami Lakes, Fla.

[21] Appl. No.: 550,532

[22] Filed: Oct. 30, 1995

[51] Int. Cl.⁶ .................................................. A61B 5/00
[52] U.S. Cl. ......................... 600/585; 600/433; 600/434; 604/95; 604/280
[58] Field of Search ................................... 128/772, 657, 128/658; 604/95, 96, 280–283

[56] References Cited

U.S. PATENT DOCUMENTS

| | | |
|---|---|---|
| Re. 33,911 | 5/1992 | Samson et al. . |
| 3,528,406 | 9/1970 | Jeckel et al. . |
| 3,547,103 | 12/1970 | Cook . |
| 3,706,883 | 12/1972 | McIntyre . |
| 3,789,841 | 2/1974 | Antoshkiw . |
| 3,847,157 | 11/1974 | Caillouette et al. . |
| 4,279,252 | 7/1981 | Martin . |
| 4,538,622 | 9/1985 | Samson et al. . |
| 4,545,390 | 10/1985 | Leary . |
| 4,554,929 | 11/1985 | Samson et al. . |
| 4,616,653 | 10/1986 | Samson et al. . |
| 4,669,465 | 6/1987 | Moore et al. . |
| 4,723,936 | 2/1988 | Buchbinder et al. . |
| 4,732,163 | 3/1988 | Bonello et al. . |
| 4,748,986 | 6/1988 | Morrison et al. . |
| 4,763,647 | 8/1988 | Gambale . |
| 4,798,598 | 1/1989 | Bonello et al. . |
| 4,830,023 | 5/1989 | de Toledo et al. . |
| 4,832,047 | 5/1989 | Sepetka et al. . |
| 4,846,186 | 7/1989 | Box et al. . |
| 4,867,173 | 9/1989 | Leoni . |
| 4,884,573 | 12/1989 | Wijay et al. . |
| 4,884,579 | 12/1989 | Engelson . |
| 4,922,924 | 5/1990 | Gambale et al. . |
| 4,925,445 | 5/1990 | Sakamoto et al. . |
| 4,940,062 | 7/1990 | Hampton et al. . |
| 5,063,935 | 11/1991 | Gambale . |
| 5,069,226 | 12/1991 | Yamauchi et al. . |
| 5,129,890 | 7/1992 | Bates et al. . |
| 5,131,407 | 7/1992 | Ischinger et al. . |
| 5,144,959 | 9/1992 | Gambale et al. . |
| 5,176,149 | 1/1993 | Grenouillet . |
| 5,178,158 | 1/1993 | De Toledo .............................. 128/657 |
| 5,209,730 | 5/1993 | Sullivan ..................................... 609/96 |
| 5,213,111 | 5/1993 | Cook et al. . |
| 5,228,453 | 7/1993 | Sepetka . |
| 5,241,970 | 9/1993 | Johlin, Jr. et al. . |
| 5,253,653 | 10/1993 | Daigle et al. . |
| 5,259,393 | 11/1993 | Corso, Jr. et al. . |
| 5,267,574 | 12/1993 | Viera et al. . |
| 5,345,945 | 9/1994 | Hodgson et al. . |
| 5,353,808 | 10/1994 | Viera . |
| 5,368,049 | 11/1994 | Raman et al. . |
| 5,402,799 | 4/1995 | Colon et al. . |
| 5,406,960 | 4/1995 | Corso, Jr. . |
| 5,409,004 | 4/1995 | Sloan . |
| 5,409,015 | 4/1995 | Palermo . |
| 5,514,128 | 5/1996 | Hillsman et al. ............................ 606/7 |
| 5,606,981 | 3/1997 | Tartacower et al. ..................... 128/657 |

FOREIGN PATENT DOCUMENTS

| | | |
|---|---|---|
| 0142330 | 5/1985 | European Pat. Off. . |
| 0223179 | 11/1986 | European Pat. Off. . |
| 2401668 | 8/1977 | France . |
| 9308862 | 5/1993 | WIPO . |

*Primary Examiner*—Max Hindenburg
*Assistant Examiner*—Pamela L. Wingood
*Attorney, Agent, or Firm*—Thomas R. Vigil; Dean Garner; Henry Collins

[57] ABSTRACT

The guidewire comprises: a tip section including a core wire including a first tapered portion, a reduced-in-diameter portion, a second tapered portion and a rod end portion, two or more highly radiopaque annular marker bands being received on the core wire between the first tapered portion and the rod end portion and precisely spaced apart on the core wire by one or more plastic tubing segments, and an outer sleeve covering said marker bands and tubing segments.

16 Claims, 1 Drawing Sheet

GUIDEWIRE WITH RADIOPAQUE MARKERS

BACKGROUND OF THE INVENTION

1. Field of the Invention.

The present invention relates to a guidewire assembly with radiopaque markers which are defined by highly radiopaque, bands or coils made of a suitable radiopaque material, such as, platinum iridium, platinum nickel or platinum tungsten and are spaced apart predetermined distances by plastic, e.g. polyimide, tubing segments located in a tip section of the guidewire assembly.

2. Description of the related art including information disclosed under 37 CFR §§ 1.97–1.99.

Heretofore numerous guidewires have been proposed with radiopaque markers. Examples of these previously proposed guidewires with marker bands are disclosed in the following prior art U.S. and foreign patents:

| U.S. Pat. No. | Patentee |
| --- | --- |
| 3,706,883 | McIntyre |
| 4,884,579 | Engelson |
| 4,922,924 | Gambale et al. |
| 5,063,935 | Gambale |
| 5,144,959 | Gambale et al. |
| 5,174,302 | Palmer |
| 5,213,111 | Cook et al. |
| 5,253,653 | Daigle et al. |
| 5,259,393 | Corso, Jr. et al. |
| 5,267,574 | Viera et al. |
| 5,353,808 | Viera |
| 5,402,799 | Colon et al. |
| 5,406,960 | Corso, Jr. |
| Foreign Publications: | |
| WO 93/08862 | Daigle, et al. |

The patents referred to above disclose various forms of marker bands that are provided in a guidewire.

For example, the Daigle et al. U.S. Pat. No. 5,253,653 discloses radiopaque rings which serve as markers which are mounted on a necked down portion of a core wire just proximal to a tip of a guidewire. The markers are held to the smaller diameter section of the guidewire by an adhesive, welding, soldering or brazing. In one embodiment the markers are interspersed between coil segments of a coiled wire.

The use of radiopaque coils interspersed between nonradiopaque coils in a coiled wire guidewire is disclosed in the Palmer U.S. Pat. No. 5,174,302.

As will be described in greater detail hereinafter, in the guidewire assembly of the present invention, highly radiopaque marker bands are spaced apart predetermined distances on a cylindrical portion of a core wire or on a tapered portion of a core wire by plastic, e.g. polyimide, tubing segments having predetermined precise lengths and with the bands and tubing segments having a polytetrafluoroethylene sleeve thereover.

SUMMARY OF THE INVENTION

According to the present invention there is provided a guidewire comprising: a tip section including a core wire including a first tapered portion, a reduced-in-diameter portion, a second tapered portion and a rod end portion, two or more highly radiopaque annular marker bands being received on the core wire between the first tapered portion and the rod end portion and precisely spaced apart on the core wire by one or more plastic tubing segments, and an outer sleeve covering the marker bands and tubing segments.

DESCRIPTION OF THE PREFERRED EMBODIMENT(S)

Figure 1:
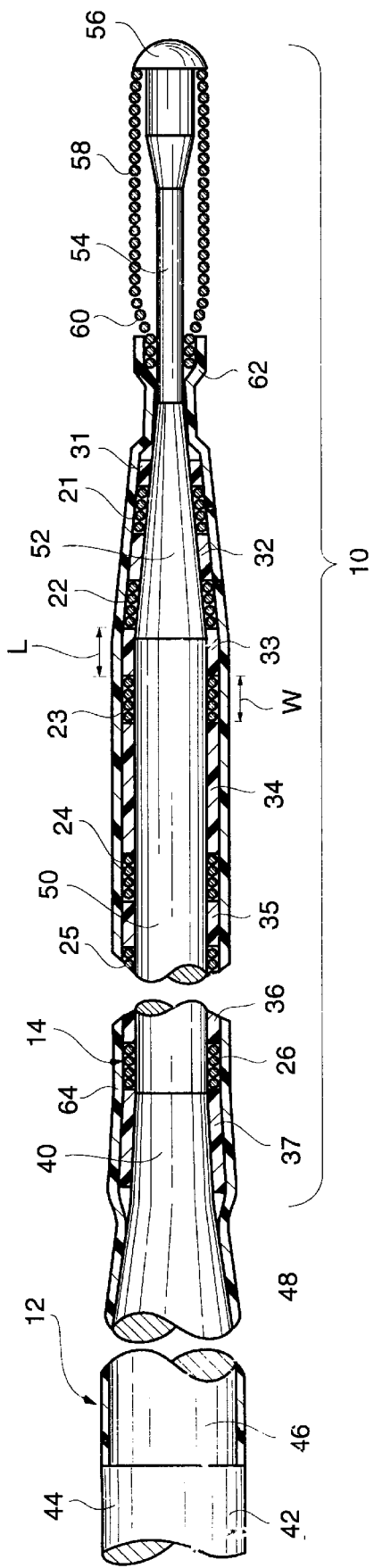
FIG. 1 is a longitudinal sectional view of a guidewire assembly with radiopaque markers constructed according to the teachings of the present invention.

Referring now to the drawings in greater detail, there is illustrated in FIG. 1 a longitudinal sectional view of a tip section 10 of a guidewire 12 having highly radiopaque markers 14 which can be defined by platinum iridium, platinum nickel or platinum tungsten coiled wire segments 21–26 precisely spaced apart by a plurality, e.g. five or more, polyimide tubing segments 31–37 mounted on a stainless steel core wire 40 which includes a primary body portion 42 having a polytetrafluoroethylene coating 44 thereon, a slightly reduced-in-diameter portion 46, a first tapered portion 48, a more reduced-in-diameter portion 50, a second tapered portion 52 tapering down to an end rod portion 54 that extends to and is connected to the distal tip 56 of the core wire 40.

Typically, nine (9) marker-bands 14 are used separated by ten (10) tubing segments.

Each marker band 14 can be 1 mm to 3 mm with 1.5 mm being a preferred width W for each band 14.

Each tubing segment spacer 31, 32 and 33 has a width L between 5 mm and 20 mm with 1 cm being a preferred width L. One or more segments, e.g. segment 34, can be 4 cm.

A platinum tungsten coiled wire 58, which is fused or welded to the distal tip 56 of the core wire 40, extends proximally to a necked down coiled wire portion 60 that ends in a reduced-in-diameter proximal coiled wire portion 62 that is received over the end rod portion 54 and held thereto by a heat shrunk polytetrafluoroethylene sleeve 64 that is heat shrunk over the proximal coiled wire portion 62, the tubing segments 31–37 and the highly radiopaque, e.g., platinum iridium, coil wire segments 21–26. The sleeve 64 extends proximally from the proximal coiled wire portion 62 to the slightly reduced-in-diameter portion 46.

The radiopaque coil wire segments 21–26 can be made of a platinum alloy including 90% platinum and 10% iridium. Alternatively, solid bands 70 (FIG. 3) of 90% platinum and 10% iridium material can be used in place of coiled wire segments 21–26.

While polyimide is a preferred plastic for the tubing segments 31–37, other plastics can be utilized including polyurethane and polyvinylchloride (PVC).

According to the teachings of the present invention, the first three tubing segments 31–33 each have a length of approximately 1 cm whereas the tubing segment 34 has a length of approximately 4 cm. The segments 31–37 can be between 1 cm and 8 cm.

Figure 2:
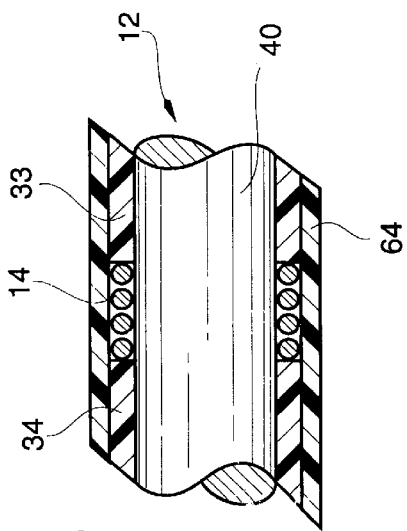
FIG. 2 is an enlarged, fragmentary, longitudinal sectional view of a radiopaque coil wire segment precisely located between two polyimide tubing segments.

One, namely coiled wire segment 24 of the radiopaque coiled wire segments 21–26, is shown in an enlarged view in FIG. 2 spaced between tubing segments 34 and 33.

Figure 3:
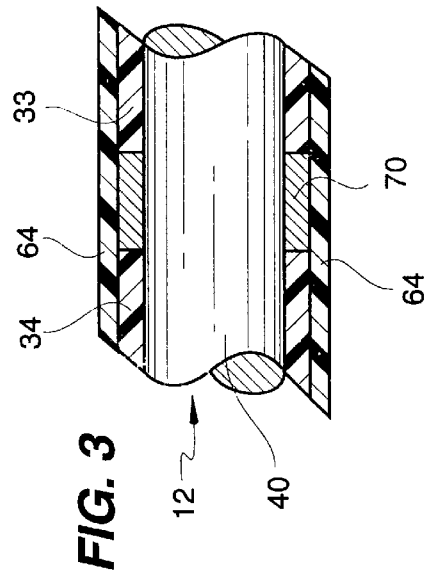
FIG. 3 is an enlarged, fragmentary, longitudinal sectional view of a radiopaque band precisely located between two polyimide tubing segments.

As shown in FIG. 3, the radiopaque 70 can be utilized in place of the radiopaque coiled wire segments 21–26.

The use of the tubing segments or spacers 31–37 interspersed between radiopaque coiled wire segments or bands 21–27 or 70, provides for a tip section 10 in a guidewire 12 which has highly radiopaque markers 14 (21–27 or 70) spaced apart by highly non-radiopaque tubing segments 31–37 thereby to provide a tip section 10 with highly visible radiopaque markers 14 (21–27 or 70) precisely spaced apart within the tip section 10 of the guidewire 12.

From the foregoing description, it will be apparent that the tip section 10 of the guidewire 12 constructed according to the teachings of the present invention has a number of advantages, some of which have been described above and others of which are inherent in the invention. For example, the spacers 31–37 and marker bands 14 provide a continuous surface whereby the outer surface of sleeve 21 is smooth without bumps. Also, modifications can be made to the tip section 10 having radiopaque markers 14 and tubing segments 31–37 without departing from the teachings of the invention. For example, spacers 31 and 37 can be omitted. Accordingly, the scope of the invention is only to be limited as necessitated by the accompanying claims.

I claim:

1. A guidewire comprising: a tip section including a core wire including a first tapered portion, a reduced-in-diameter portion, a second tapered portion and a rod end portion, at least three highly radiopaque annular marked bands having a length between 1 mm and 3 mm which are received on said core wire between said first tapered portion and said rod end portion, said middle band being received on said core wire, and precisely spaced apart on said core wire by at least two plastic sleeves each having a precise length between 5 mm and 8 cm, the precise length being the same or different for the two plastic sleeves, and an outer sleeve covering the marker bands and tubing segments or sleeves.

2. The guidewire of claim 1 wherein said annular marker bands are made of platinum iridium coiled wire segments.

3. The guidewire of claim 1 wherein said annular marker bands are made of platinum iridium solid annular bands.

4. The guidewire of claim 1 wherein said plastic sleeves are made of polyimide.

5. The guidewire of claim 1 wherein said outer sleeve is made of polytetrafluorethylene.

6. The guidewire of claim 1 wherein said three marker bands are spaced apart by two plastic sleeves each having a length between approximately 5 mm and 8 cm.

7. The guidewire of claim 6 where said length of said most distal tubing segment is approximately 1 cm.

8. The guidewire of claim 6 wherein the proximal one of the three marker bands is spaced from the next proximal marker band by a plastic sleeve having a length of approximately 1 cm to 8 cm.

9. The guidewire of claim 1 wherein said marker bands are made of platinum iridium bands having approximately 90% platinum and 10% iridium.

10. The guidewire of claim 1 wherein said marker bands are annular rings.

11. The guidewire of claim 1 wherein each marker band has a length and of approximately 1.5 mm.

12. The guidewire of claim 1 including between 2 to 15 marker bands.

13. The guidewire of claim 12 including between 1 to 17 tubing segments.

14. The guidewire of claim 1 wherein said core wire is made of stainless steel.

15. The guidewire of claim 1 wherein said annular marker bands are made of platinum nickel.

16. The guidewire of claim 1 wherein said annular marker bands are made of platinum tungsten.

* * * * *